(12) United States Patent
Li

(10) Patent No.: US 6,733,505 B2
(45) Date of Patent: May 11, 2004

(54) APPARATUS AND METHOD FOR LOADING A PROSTHETIC NUCLEUS INTO A DEPLOYMENT CANNULA TO REPLACE THE NUCLEUS PULPOSUS OF AN INTERVERTEBRAL DISC

(75) Inventor: Lehmann K. Li, Milford, CT (US)

(73) Assignee: SDGI Holdings, Inc., Wilmington, DE (US)

( * ) Notice: Subject to any disclaimer, the term of this patent is extended or adjusted under 35 U.S.C. 154(b) by 1 day.

(21) Appl. No.: 09/998,978

(22) Filed: Nov. 15, 2001

(65) Prior Publication Data

US 2002/0123808 A1 Sep. 5, 2002

Related U.S. Application Data

(63) Continuation-in-part of application No. 10/011,916, filed on Nov. 5, 2001, which is a continuation-in-part of application No. 09/559,899, filed on Apr. 26, 2000.
(60) Provisional application No. 60/248,807, filed on Nov. 15, 2000.

(51) Int. Cl.[7] .................................................. A61F 2/00
(52) U.S. Cl. ........................ 606/99; 623/908; 623/923
(58) Field of Search ........................ 623/17.12, 17.16, 623/902, 920, 908, 923; 606/99, 107

(56) References Cited

U.S. PATENT DOCUMENTS

| 3,875,595 | A | * | 4/1975 | Froning ................. 623/17.12 |
|---|---|---|---|---|
| 4,157,085 | A | | 6/1979 | Austad |
| 4,573,998 | A | | 3/1986 | Mazzocco |
| 5,005,591 | A | | 4/1991 | Austad |
| 5,171,280 | A | | 12/1992 | Baumgartner |
| 5,534,028 | A | | 7/1996 | Bao et al. |
| 5,562,736 | A | | 10/1996 | Ray et al. |
| 5,674,295 | A | | 10/1997 | Ray et al. |
| 5,674,296 | A | | 10/1997 | Bryan et al. |
| 5,711,317 | A | * | 1/1998 | McDonald ................. 606/107 |
| 6,132,465 | A | | 10/2000 | Ray et al. |
| 6,280,449 | B1 | | 8/2001 | Blake |

FOREIGN PATENT DOCUMENTS

WO    WO 00/64385 A1    11/2000

* cited by examiner

*Primary Examiner*—Bruce Snow
*Assistant Examiner*—Brian E Pellegrino
(74) *Attorney, Agent, or Firm*—Woodard, Emhardt, Moriarty, McNett & Henry LLP

(57) ABSTRACT

An apparatus comprising a carrier cartridge, a deployment cannula releasably connected to the carrier cartridge, a folding die, and one or more force application members. A force applied on a prosthetic nucleus by the force application members in the direction of the carrier cartridge toward the deployment cannula causes the prosthetic nucleus to move through the folding die and become loaded into the deployment cannula. The distal end of the cannula is placed into the chamber of the intervertebral disc and the prosthetic nucleus is ejected from the deployment cannula so as to implant the prosthetic nucleus in the chamber of the intervertebral disc.

27 Claims, 4 Drawing Sheets

APPARATUS AND METHOD FOR LOADING A PROSTHETIC NUCLEUS INTO A DEPLOYMENT CANNULA TO REPLACE THE NUCLEUS PULPOSUS OF AN INTERVERTEBRAL DISC

REFERENCE TO PENDING PRIOR PATENT APPLICATIONS

This patent application claims benefit of pending prior U.S. Provisional Patent Application Ser. No. 60/248,807, filed Nov. 15, 2000 by Lehmann K. Li for PANCAKE DISC DELIVERY METHOD AND APPARATUS, which patent application is hereby incorporated herein by reference, and is a continuation-in-part of pending prior U.S. patent application Ser. No. 09/559,899, filed Apr. 26, 2000 by Lehmann K. Li et al. for PROSTHETIC APPARATUS AND METHOD, which patent application is hereby incorporated herein by reference, and is a continuation-in-part of pending prior U.S. patent application Ser. No. 10/011,916 filed Nov. 5, 2001 by Lehmann K. Li et al. for APPARATUS AND METHOD FOR REPLACING THE NUCLEUS PULPOSUS OF AN INTERVERTEBRAL DISC OR FOR REPLACING AN ENTIRE INTERVERTEBRAL DISC, which patent application is hereby incorporated herein by reference.

FIELD OF THE INVENTION

This invention relates to surgical apparatus and methods in general, and more particularly to surgical apparatus and methods for the repair and/or replacement of the nucleus pulposus of an intervertebral disc.

BACKGROUND OF THE INVENTION

The spinal column is a flexible chain of closely linked vertebral bodies. In a normal human spine, there are seven cervical, twelve thoracic and five lumbar vertebral bodies. Below the lumbar vertebrae are the sacrum and coccyx. Each individual vertebral body has an outer shell of hard, dense bone. Inside the vertebral body is a honeycomb of cancellous bone containing red bone marrow. All of the red blood cells, and many of the white blood cells, are generated inside such cancellous bone, where the blood cells mature before being released into the blood stream.

The intervertebral disc, which is also known as the spinal disc, serves as a cushion between the vertebral bodies so as to permit controlled motion. A healthy intervertebral disc consists of three components: a gelatinous inner core called the nucleus pulposus (or, more simply, the nucleus); a series of overlapping and laminated plies of tough fibrous rings called the annulus fibrosus (or, more simply, the annulus); and two (i.e., superior and inferior) thin cartilage layers, connecting the intervertebral disc to the thin cortical bone of the adjacent vertebral bodies, called the end plates.

An intervertebral disc may be displaced and/or damaged due to trauma (such as a herniated disc), or disease (such as a degenerative disc disease).

A herniated disc may bulge out and compress itself onto a nerve, resulting in lower leg pain, loss of muscle control or paralysis. To treat a herniated disc, the offending portions of the disc (i.e., the bulging portions of the nucleus) are generally removed surgically.

A degenerative disc disease typically causes the disc to gradually reduce in height, causing the annulus to buckle, tear or separate, radially and/or circumferentially, and causing persistent and disabling back pain. Degenerative disc disease is generally treated by surgically removing the nucleus and fusing together the adjacent vertebral bodies so as to stabilize the joint.

In either case, whether removing some or all of the nucleus, these procedures ultimately place greater stress on adjacent discs due to their need to compensate for the lack of motion. This may in turn cause premature degeneration of those adjacent discs.

Modern trends in surgery include the restoration, rather than the removal, of anatomical structures, with this restoration preferably being effected through the use of minimally invasive surgical techniques. The ability to surgically repair damaged tissues or joints, creating as few and as small incisions as possible, generally produces less trauma and pain for the patient while yielding better clinical outcomes.

In this respect it has been recognized that it may be possible to replace a damaged nucleus pulposus with a prosthetic implant, whereby to restore the spinal disc to its original configuration and function. Unfortunately, however, such implants, sometimes referred to as a "prosthetic nucleus", tend to suffer from a variety of deficiencies.

A deficiency of current prosthetic nuclei is that they generally require relatively large or multiple incisions in the annulus in order to insert the prosthetic nucleus into the interior of the spinal disc. Such large or multiple incisions tend to further weaken an already compromised disc. Additionally, these incisions in the annulus are generally not easily repaired; thus, there can be a concern that the prosthetic nucleus may eventually work its way back out of the disc space and interfere with the surrounding anatomy.

A further deficiency of current, less-invasive prosthetic nuclei (see, for example, U.S. Pat. No. 5,674,295, issued Oct. 07, 1997 to Ray et al.) is that multiple, laterally-spaced implants typically have to be used to recreate the nucleus, which suggests that the side-by-side positioning of the several implants has to be carefully considered so as to ensure proper carrying of the load.

In pending prior U.S. patent application Ser. No. 09/559, 899, filed Apr. 26, 2000 by Lehmann K. Li et al. for PROSTHETIC APPARATUS AND METHOD, which patent application is hereby incorporated herein by reference, and pending prior U.S. patent application Ser. No. 10/011,916, filed Nov. 05, 2001 by Lehmann K. Li et al. for APPARATUS AND METHOD FOR REPLACING THE NUCLEUS PULPOSUS OF AN INTERVERTEBRAL DISC OR FOR REPLACING AN ENTIRE INTERVERTEBRAL DISC, which patent application is hereby incorporated herein by reference, there are disclosed various prosthetic nuclei which, among other things, may be mechanically reshaped (e.g., by rolling, curling and/or folding) into a reduced footprint prior to deployment within the interior of the disc, whereupon it is restored to its original shape.

With this in mind, it would be advantageous to provide an apparatus and method for use in mechanically reshaping a prosthetic nucleus with a reduced footprint prior to deployment within the interior of the disc.

SUMMARY OF THE INVENTION

Accordingly, one object of the present invention is to provide improved apparatus for replacing the nucleus pulposus of an intervertebral disc.

Another object of the present invention is to provide an improved method for replacing the nucleus pulposus of an intervertebral disc.

And another object of the present invention is to provide improved apparatus for delivering a prosthetic nucleus into the inner portion of an intervertebral disc space.

Still another object of the present invention is to provide an improved method for delivering a prosthetic nucleus into the inner portion of an intervertebral disc space.

And still another object of the present invention is to provide improved apparatus for loading a prosthetic nucleus into a deployment cannula.

Yet still another object of the present invention is to provide an improved method for loading a prosthetic nucleus into a deployment cannula.

With the above and other objects in view, a feature of the present invention is the provision of a novel apparatus for implanting a prosthetic nucleus in a chamber of an intervertebral disc after removal of at least a portion of a damaged or degenerated nucleus from the chamber, the apparatus comprising:

a carrier cartridge defining a first end and a second end, the carrier cartridge having a cavity at the first end, the cavity being configured to selectively hold the prosthetic nucleus;

a deployment cannula having a proximal end and a distal end, the distal end of the deployment cannula being configured for implanting the prosthetic nucleus in the chamber of the intervertebral disc;

releasable connection means being located on at least one of the second end of the carrier cartridge and the distal end of the deployment cannula, the releasable connection means being configured to selectively connect the carrier cartridge and deployment cannula to one another;

a folding die being configured in at least one of the carrier cartridge and the deployment cannula, the folding die forming an inwardly decreasing taper in a direction from the cavity to the deployment cannula so as to reconfigure the prosthetic nucleus from a relatively flat configuration to a substantially cylindrical configuration as the prosthetic nucleus moves from the carrier cartridge to the deployment cannula; and force applying means being configurable to impart a force on the prosthetic nucleus so as to cause the prosthetic nucleus to move from said cavity into said deployment cannula.

Another feature of the present invention is the provision of a novel apparatus for loading a prosthetic nucleus in a deployment cannula having a proximal end and a distal end, the distal end of the deployment cannula being configured for implanting the prosthetic nucleus in the chamber of the intervertebral disc, the apparatus comprising:

a carrier cartridge defining a first end and a second end, the carrier cartridge having a cavity at the first end, the cavity being configured to selectively hold the prosthetic nucleus;

releasable connection means being located on the second end of the carrier cartridge, the releasable connection means being configured to selectively connect the carrier cartridge and deployment to one another;

a folding die being configured in the carrier cartridge, the folding die forming an inwardly decreasing taper in a direction from the cavity to the deployment cannula so as to reconfigure the prosthetic nucleus from a relatively flat configuration to a substantially cylindrical configuration as the nucleus moves from the carrier cartridge to the deployment cannula; and force applying means being configurable to impart a force on the prosthetic nucleus so as to cause the prosthetic nucleus to move from the cavity into the deployment cannula.

A further feature of the present invention is the provision of a novel method for implanting a prosthetic nucleus in a chamber of an intervertebral disc after removal of at least a portion of a damaged or degenerated nucleus from the chamber, the method comprising:

providing apparatus for implanting a prosthetic nucleus in a chamber of an intervertebral disc after removal of at least a portion of a damaged or degenerated nucleus from the chamber, the apparatus comprising:

a carrier cartridge defining a first end and a second end, the carrier cartridge having a cavity at the first end, the cavity being configured to selectively hold the prosthetic nucleus;

a deployment cannula having a proximal end and a distal end, the distal end of the deployment cannula being configured for implanting the prosthetic nucleus in the chamber of the intervertebral disc;

releasable connection means being located on at least one of the second end of the carrier cartridge and the distal end of the deployment cannula, the releasable connection means being configured to selectively connect the carrier cartridge and deployment cannula to one another;

a folding die being configured in at least one of the carrier cartridge and the deployment cannula, the folding die forming an inwardly decreasing taper in a direction from the cavity to the deployment cannula so as to reconfigure the prosthetic nucleus from a relatively flat configuration to a substantially cylindrical configuration as the prosthetic nucleus moves from the carrier cartridge to the deployment cannula; and force applying means being configurable to impart a force on the prosthetic nucleus so as to cause the prosthetic nucleus to move from the cavity into the deployment cannula.

applying a force on the prosthetic nucleus in the direction of the cavity to the deployment cannula so as to cause the prosthetic nucleus to move through the folding die and become loaded into the deployment cannula;

placing the distal end of the cannula into the chamber of the intervertebral disc; and ejecting the prosthetic nucleus from the deployment cannula so as to implant the prosthetic nucleus in the chamber of the intervertebral disc.

Another further feature of the present invention is the provision of a novel method for loading a prosthetic nucleus in a deployment cannula having a proximal end and a distal end, the distal end of the deployment cannula being configured for implanting the prosthetic nucleus in a chamber of an intervertebral disc, the method comprising:

providing apparatus for loading a prosthetic nucleus in a deployment cannula, the apparatus comprising:

a carrier cartridge defining a first end and a second end, the carrier cartridge having a cavity at the first end, the cavity being configured to selectively hold the prosthetic nucleus;

releasable connection means being located on the second end of the carrier cartridge, the releasable connection means being configured to selectively connect the carrier cartridge and deployment cannula to one another;

a folding die being configured in the carrier cartridge, the folding die forming an inwardly decreasing taper in a direction from the cavity to the deployment cannula so as to reconfigure the prosthetic nucleus from a relatively flat configuration to a substantially cylindrical configuration as the prosthetic nucleus moves from the carrier cartridge to the deployment cannula; and force applying means being configurable to impart a force on the prosthetic nucleus so as to cause the prosthetic nucleus to move from the cavity into the deployment cannula; and applying a force on the prosthetic nucleus in the direction of the cavity to the deployment cannula so as to cause the prosthetic nucleus to move through the folding die and become loaded into the deployment cannula.

And another further feature of the present invention is the provision of a novel prosthetic nucleus comprising:

a body adapted to be mechanically reshaped into a reduced footprint prior to deployment within the interior of a disc, whereupon it will be restored to its original shape; and a plurality of filaments secured to the body, whereby the body may be drawn through a reshaping die and into a deployment cannula.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
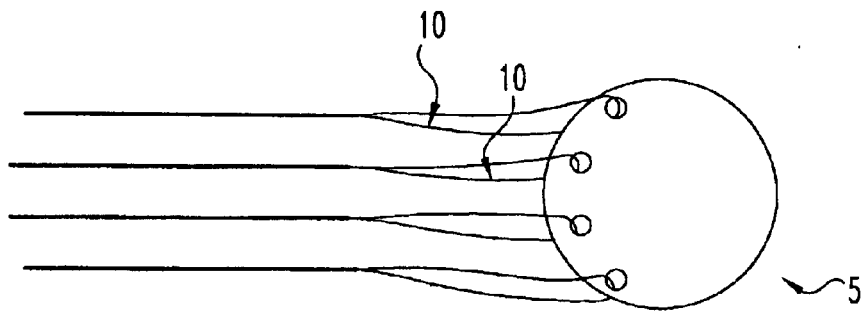
FIG. 1 is a plan view of one embodiment of a prosthetic nucleus suitable for use in association with the present invention.

Looking first at FIG. 1, in a preferred embodiment of the present invention, there is shown a prosthetic nucleus 5 with force applying means 10, which are herein shown and described as, but not limited to, one or more filaments 10. Filaments 10 are used for applying a force to position prosthetic nucleus 10. Filaments 10 may also be removably connected to prosthetic nucleus 5.

Looking at FIGS. 2–5, there is shown a carrier cartridge 15 having a cavity 20, a folding die 25 and releasable connection means 30 for selective attachment to a deployment cannula 35. Prosthetic nucleus 5 may be maintained in a relatively flat configuration in carrier cartridge 15 prior to being loaded into cannulated delivery tube 35.

Figure 2:
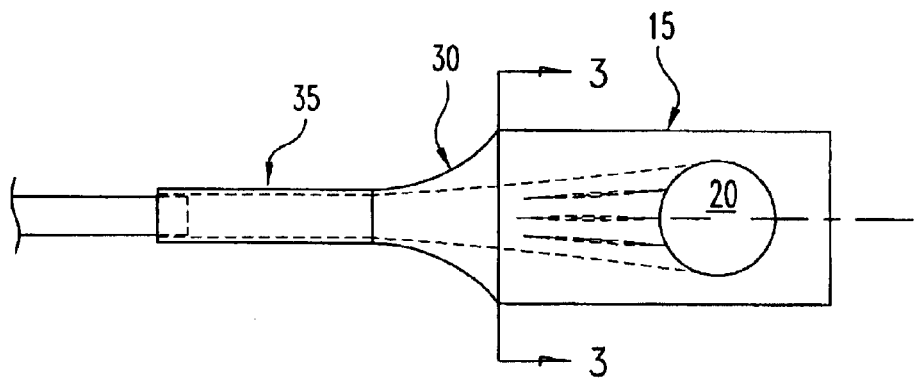
FIG. 2 is a plan view of an apparatus for implanting a prosthetic nucleus into a chamber of an intervertebral disc according to one embodiment of the present invention.
Figure 3:
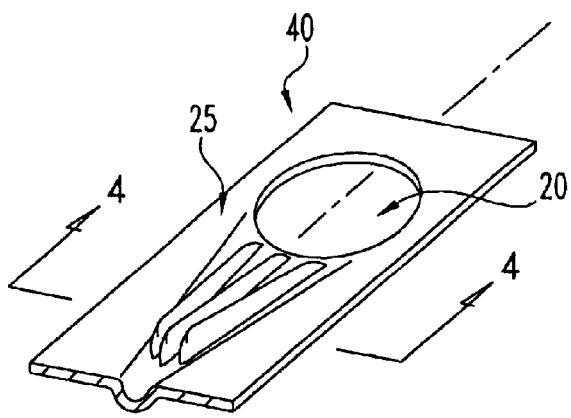
FIG. 3 is a cross-sectional perspective view of the apparatus shown in FIG. 2, as viewed along line 3—3 of FIG. 2.
Figure 4:
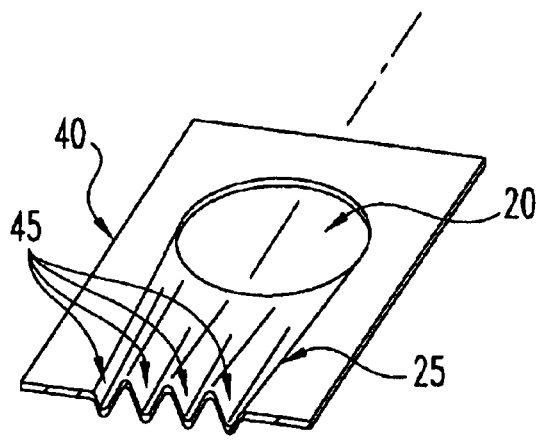
FIG. 4 is a cross-sectional perspective view of the apparatus shown in FIG. 3, as viewed along line 4—4 of FIG. 3

Referring now to FIGS. 3 and 4, which are cross-sectional views taken along lines 3—3 and 4—4 of FIGS. 2 and 3, respectively, in a preferred embodiment of the present invention, there is shown one portion 40 of carrier cartridge 15 comprising folding die 25. Another portion of carrier cartridge 15 (not shown) is configured together with portion 40 to form carrier cartridge 15. Folding die 25 is located between cavity 20 and releasable connection means 30 so as to reconfigure the orientation of prosthetic nucleus 5 from a relatively flat configuration to a relatively cylindrical configuration suitable as it passes through carrier cartridge 15 into deployment cannula 35.

In a preferred embodiment of the present invention, folding die 25 comprises grooves 45 formed along an axis from cavity 20 to releasable connection means 30. Grooves 45 act to initiate the process of reducing the cross-sectional dimensions of prosthetic nucleus 5 prior to loading within deployment cannula 35.

Figure 5:
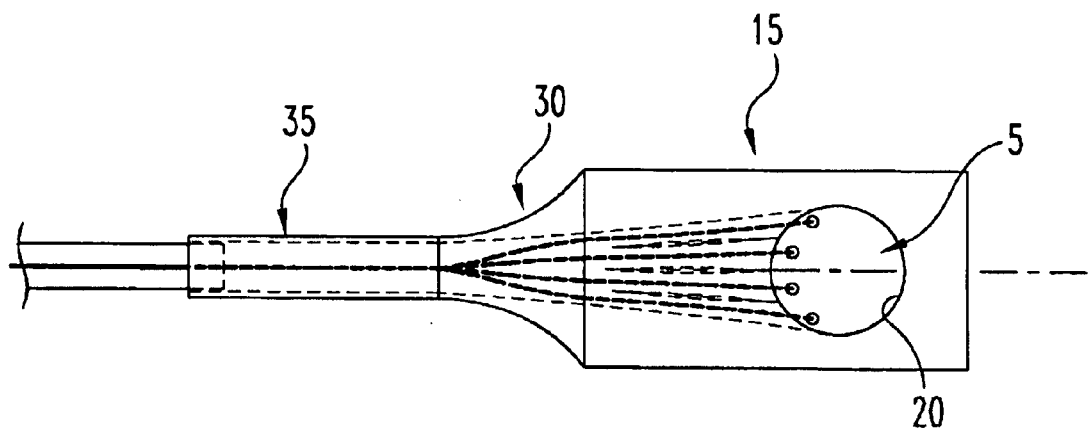
FIG. 5 is a plan view of the apparatus shown in FIG. 2 with the prosthetic nucleus disposed within a carrier cartridge portion of the apparatus.

Referring now to FIG. 5, carrier cartridge 15 and deployment cannula 35 are shown in attachment to one another prior to loading prosthetic nucleus into carrier cartridge 15. In a preferred embodiment of the present invention, this attachment is accomplished using releasable connection means 30. For example, releasable connection means 30 include, but is not limited to, a slideable connection in which carrier cartridge 15 is configured for slideable connection with deployment cannula 35, or a pre-formed connection in which carrier cartridge 15 and deployment cannula 35 are broken apart from one another after loading is completed.

Figure 6A:
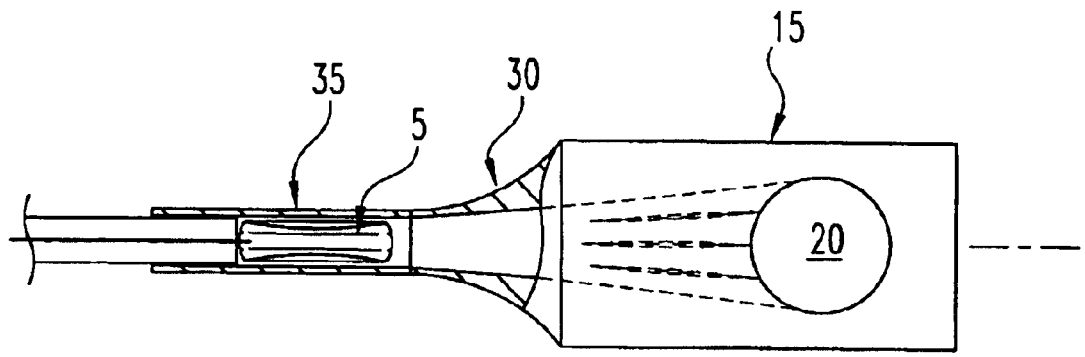
FIG. 6a is a plan view of the apparatus shown in FIG. 2, partially in cross-section, with the prosthetic nucleus disposed within a cannula portion of the apparatus.
Figure 6B:
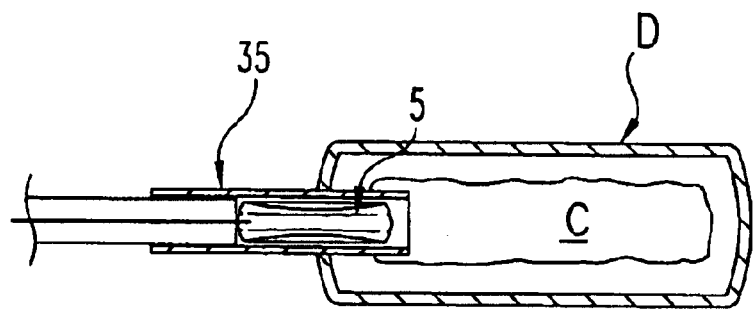
FIG. 6b is a side view of the apparatus shown in FIG. 6a, partially in cross-section, with the carrier cartridge portion of the apparatus removed from the cannula portion and with the distal end portion of the cannula portion positioned within an intervertebral disc space.

Looking at FIGS. 5, 6a and 6b, prosthetic nucleus 5 is shown positioned prior to being loaded into deployment cannula 35 (FIG. 5) and after being loaded into deployment cannula 35 (FIG. 6a). Prior to loading, filaments 10 extend through cavity 20 of carrier cartridge 15 into deployment cannula 35 (FIG. 5). Filaments 10 are then drawn away from carrier cartridge 15, though deployment cannula 35, so as to draw prosthetic nucleus 5 out of cavity 20, through folding die 25, and into deployment cannula 35 (FIG. 6a). Carrier cartridge 15 may then be removed from deployment cannula 35 (FIG. 6b) so as to leave prosthetic nucleus 5 loaded into deployment cannula 35. In this configuration, the distal end of the loaded deployment cannula 35 may be positioned within a chamber C of the disc space D (FIG. 6b) and prosthetic nucleus 5 may be ejected therefrom, e.g., with a plunger, into the disc space chamber C.

Preferably, prosthetic nucleus 5 is formed of a material which is elastic and/or swellable so as to return to its original configuration after implantation into a chamber of an intervertebral disc.

Figure 7:
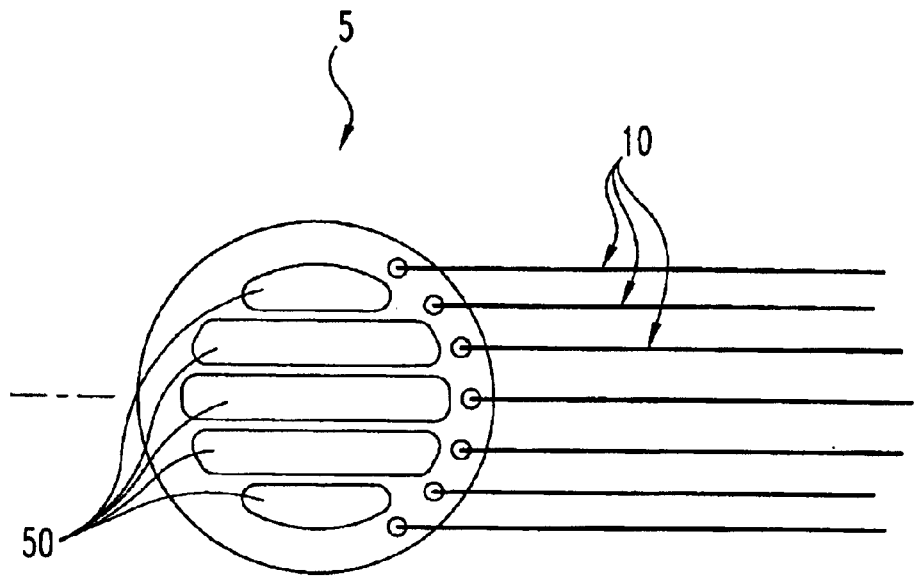
FIG. 7 is a plan view of another embodiment of a prosthetic nucleus suitable for use in association with the present invention.
Figure 8:
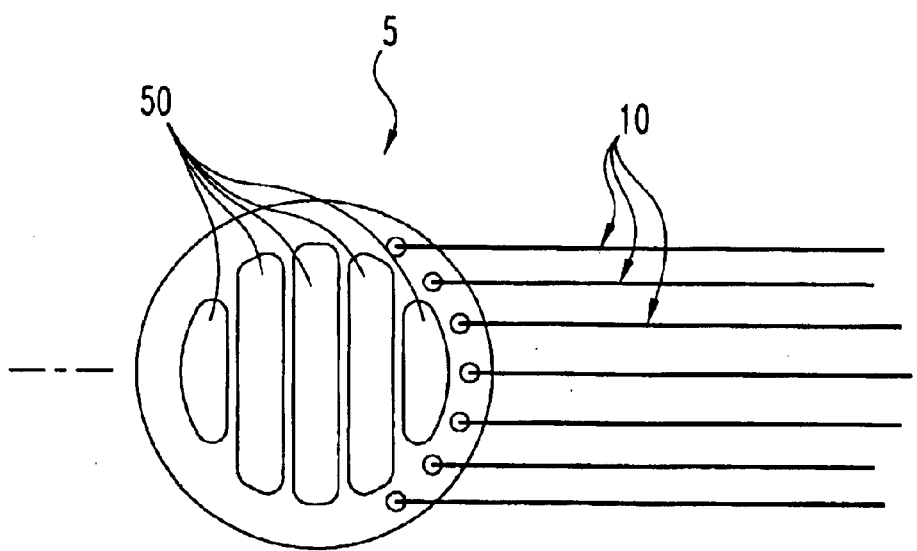
FIG. 8 is a plan view of a further embodiment of a prosthetic nucleus suitable for use in association with the present invention.

Looking now at FIGS. 7 and 8, in a preferred embodiment of the invention, there is shown ribbed sections 50 disposed on prosthetic nucleus 5. Ribbed sections 50 serve to control and/or direct post-implantation restoration and/or swelling of prosthetic nucleus 5. Ribbed sections 50 may be orientated parallel to filaments 10 (FIG. 7) or perpendicular to filaments 10 (FIG. 8).

MODIFICATIONS OF THE PREFERRED EMBODIMENTS

Prosthetic nucleus 5 may be any geometrical shape. Prosthetic nucleus 5 may have multiple internal or external surfaces (e.g., walls, barriers, supports, etc.) that may be connected to provide further stability or strength. Certain portions of the surfaces may be reinforced or made more rigid to encourage or to direct expansion so as to change the dimensions in a particular way.

Prosthetic nucleus 5 may be configured to have at least one surface folded inwardly or outwardly to accommodate reducing its size to fit through a cannula for minimally invasive delivery. Once the prosthetic nucleus 5 is positioned inside the disc space, the prosthetic nucleus 5 may change its shape due to swelling, hydration, expansion, reaction or by other means.

Prosthetic nucleus 5 may be encased in or attached to at least a second member. The second member may be of a weave pattern, or of a material which permits, assists or directs the elastic member to act in certain defined ways or directions.

Prosthetic nucleus 5 may be a casing, into which some material is placed either before delivery of the member or after delivery of the member into the disc space. Conversely, prosthetic nucleus 5 may be placed into another member, either prior to or after delivery of the prosthetic nucleus 5 into the disc space.

Grooves 45 may curl or roll the prosthetic nucleus 5 in addition to, or instead of, simply folding the prosthetic nucleus 5. Grooves 45 also may be situated within deployment cannula 35 instead of in a carrier cartridge 15.

The force to position prosthetic nucleus 5 in the deployment cannula 35, including the force applying means, may be a pulling, pushing or rotating force.

ADVANTAGES OF THE INVENTION

An advantage of the invention is that only a small insertion port is required to implant a prosthetic nucleus, thus minimizing the trauma to the annulus. The prosthetic nucleus may also be of a larger size than the opening through with the prosthetic nucleus must pass. The prosthetic nucleus may be packaged as a flat device for easier assembly, packaging and handling purposes. In this configuration, the prosthetic nucleus is less likely to develop a bias or shape memory as opposed to being housed in a tube for an extended period of time, including, for example, shipping and storage.

What is claimed is:

1. Apparatus for implanting a prosthetic nucleus in a chamber of an intervertebral disc after removal of at least a portion of a damaged or degenerated nucleus from the chamber, said apparatus comprising:

a carrier cartridge defining a first end and a second end, said carrier cartridge having a cavity at said first end, said cavity being configured to selectively hold said prosthetic nucleus;

a deployment cannula having a proximal end and a distal end, said distal end of said deployment cannula being configured for implanting said prosthetic nucleus in the chamber of the intervertebral disc;

releasable connection means being located on at least one of said second end of said carrier cartridge and said distal end of said deployment cannula, said releasable connection means being configured to selectively connect said carrier cartridge and deployment cannula to one another;

a folding die being configured in at least one of said carrier cartridge and said deployment cannula, said folding die forming an inwardly decreasing taper in a direction from said cavity to said deployment cannula so as to reconfigure said prosthetic nucleus from a relatively flat configuration to a substantially cylindrical configuration as said prosthetic nucleus moves from said carrier cartridge to said deployment cannula; and force applying means being configurable to impart a force on said prosthetic nucleus so as to cause said prosthetic nucleus to move from said cavity into said deployment cannula.

2. Apparatus according to claim 1 wherein said releasable connection means are located on said second end of said carrier cartridge.

3. Apparatus according to claim 1 wherein said releasable connection means are located on said distal end of said deployment cannula.

4. Apparatus according to claim 1 wherein said releasable connection means are located on each of said second end of said carrier cartridge and said distal end of said deployment cannula.

5. Apparatus according to claim 1 wherein said releasable connection means comprise a slideably configured connection between said carrier cartridge and said deployment cannula.

6. Apparatus according to claim 1 wherein said releasable connection means comprise a breakable connection between said carrier cartridge and said deployment cannula.

7. Apparatus according to claim 1 wherein said folding die is configured in said carrier cartridge.

8. Apparatus according to claim 1 wherein said carrier cartridge and said deployment cannula are pre-formed together with said prosthetic nucleus being pre-loaded in said cavity of said carrier cartridge.

9. Apparatus according to claim 1 wherein said carrier cartridge comprises a first half and a second half, wherein said first half and said second half are configurable in selective engagement to one another so as to permit access to an interior portion of said cavity.

10. Apparatus according to claim 1 wherein said folding die further comprises a series of grooves therein.

11. Apparatus according to claim 1 wherein said folding die is configured to fold said prosthetic nucleus.

12. Apparatus according to claim 1 wherein said force applying means comprise at least one filament in selective attachment to said prosthetic nucleus, whereby pulling said at least one filament through said deployment cannula in the direction from said cavity toward said deployment cannula causes said prosthetic nucleus to move from said cavity into said deployment cannula.

13. Apparatus according to claim 1 wherein said force applying means exerts a pulling force applied in the direction of said first end to second end of said carrier cartridge.

14. Apparatus for loading a prosthetic nucleus in a deployment cannula having a proximal end and a distal end, said distal end of said deployment cannula being configured for implanting said prosthetic nucleus in the chamber of the intervertebral disc, said apparatus comprising:

a carrier cartridge defining a first end and a second end, said carrier cartridge having a cavity at said first end, said cavity being configured to selectively hold said prosthetic nucleus; releasable connection means being located on said second end of said carrier cartridge, said releasable connection means being configured to selectively connect said carrier cartridge and said deployment cannula to one another; a folding die being configured in said carrier cartridge, said folding die forming an inwardly decreasing taper in a direction from said cavity to said deployment cannula so as to reconfigure said prosthetic nucleus from a relatively flat configuration to a substantially cylindrical configuration as said nucleus moves from said carrier cartridge to said deployment cannula; and force applying means being configurable to impart a force on said prosthetic nucleus so as to cause said prosthetic nucleus to move from said cavity into said deployment cannula.

15. Apparatus according to claim 14 wherein said releasable connection means are located on said second end of said carrier cartridge.

16. Apparatus according to claim 14 wherein said releasable connection means are located on each of said second end of said carrier cartridge and said distal end of said deployment cannula.

17. Apparatus according to claim 14 wherein said releasable connection means comprise a slideably configured connection between said carrier cartridge and said deployment cannula.

18. Apparatus according to claim 14 wherein said releasable connection means comprise a breakable connection between said carrier cartridge and said deployment cannula.

19. Apparatus according to claim 14 wherein said folding die is configured in said carrier cartridge.

20. Apparatus according to claim 14 wherein said carrier cartridge is pre-formed with said prosthetic nucleus pre-loaded in said cavity therein.

21. Apparatus according to claim 14 wherein said carrier cartridge comprises a first half and a second half, wherein said first half and said second half are configurable in selective engagement to one another so as to permit access to an interior portion of said cavity.

22. Apparatus according to claim 14 wherein said folding die further comprises a series of grooves therein.

23. Apparatus according to claim 14 wherein said folding die is configured to fold said prosthetic nucleus.

24. Apparatus according to claim 14 wherein said force applying means comprise at least one filament in selective attachment to said prosthetic nucleus, whereby pulling said at least one filament through said deployment cannula in the direction from said cavity toward said deployment cannula causes said prosthetic nucleus to move from said cavity into said deployment cannula.

25. Apparatus according to claim 14 wherein said force applying means exerts a pulling force applied in the direction of said first end to said second end of said carrier cartridge.

26. A method for implanting a prosthetic nucleus in a chamber of an intervertebral disc after removal of at least a portion of a damaged or degenerated nucleus from the chamber, said method comprising:

providing apparatus for implanting a prosthetic nucleus in a chamber of an intervertebral disc after removal of at least a portion of a damaged or degenerated nucleus from the chamber, said apparatus comprising:

a carrier cartridge defining a first end and a second end, said carrier cartridge having a cavity at said first end, said cavity being configured to selectively hold said prosthetic nucleus;

a deployment cannula having a proximal end and a distal end, said distal end of said deployment cannula being configured for implanting said prosthetic nucleus in the chamber of the intervertebral disc;

releasable connection means being located on at least one of said second end of said carrier cartridge and said distal end of said deployment cannula, said releasable connection means being configured to selectively connect said carrier cartridge and deployment cannula to one another;

a folding die, said folding die forming an inwardly decreasing taper in a direction from said cavity to said deployment cannula so as to reconfigure said prosthetic nucleus from a relatively flat configuration to a substantially cylindrical configuration as said prosthetic nucleus moves from said carrier cartridge to said deployment cannula; and force applying means being configurable to impart a force on said prosthetic nucleus so as to cause said prosthetic nucleus to move from said cavity into said deployment cannula;

applying a force on said prosthetic nucleus in the direction of said cavity to said deployment cannula so as to cause said prosthetic nucleus to move through said folding die and become loaded into said deployment cannula;

disconnecting said carrier cartridge from said deployment cannula;

placing said distal end of said cannula into the chamber of the intervertebral disc; and ejecting said prosthetic nucleus from said deployment cannula so as to implant said prosthetic nucleus in the chamber of the intervertebral disc.

27. A method for loading a prosthetic nucleus in a deployment cannula having a proximal end and a distal end, said distal end of said deployment cannula being configured for implanting said prosthetic nucleus in a chamber of an intervertebral disc, said method comprising:

providing apparatus for loading a prosthetic nucleus in a deployment cannula, said apparatus comprising:

a carrier cartridge defining a first end and a second end, said carrier cartridge having a cavity at said first end, said cavity being configured to selectively hold said prosthetic nucleus;

releasable connection means being located on said second end of said carrier cartridge, said releasable connection means being configured to selectively connect said carrier cartridge and deployment cannula to one another;

a folding die being configured in said carrier cartridge, said folding die forming an inwardly decreasing taper in a direction from said cavity to said deployment cannula so as to reconfigure said prosthetic nucleus from a relatively flat configuration to a substantially cylindrical configuration as said prosthetic nucleus moves from said carrier cartridge to said deployment cannula; and force applying means being configurable to impart a force on said prosthetic nucleus so as to cause said prosthetic nucleus to move from said cavity into said deployment cannula; and applying a force on said prosthetic nucleus in the direction of said cavity to the deployment cannula so as to cause said prosthetic nucleus to move through said folding die and become loaded into the deployment cannula; and disconnecting said carrier cartridge from said deployment cannula.

* * * * *